United States Patent [19]

Belilos

[11] Patent Number: 4,952,369
[45] Date of Patent: Aug. 28, 1990

[54] ULTRAVIOLET DEVICE AND ITS USE

[76] Inventor: Moshe Belilos, 43 Ben Gurion Street, Bat Yam, Israel

[21] Appl. No.: 177,639

[22] Filed: Apr. 5, 1988

[30] Foreign Application Priority Data

Feb. 16, 1988 [IL] Israel ........................................ 85430

[51] Int. Cl.⁵ ............................ A61L 2/10; F21L 1/00
[52] U.S. Cl. ........................................ 422/24; 362/157; 362/194
[58] Field of Search ................... 422/24; 362/157, 194

[56] References Cited

U.S. PATENT DOCUMENTS

| | | | |
|---|---|---|---|
| 1,965,947 | 7/1934 | Prouty | 422/24 |
| 2,397,757 | 4/1946 | Schwedersky | 422/24 |
| 2,413,494 | 12/1946 | Fortney | 422/24 |
| 4,317,996 | 3/1982 | Davis | 250/302 |

Primary Examiner—Robert J. Warden
Assistant Examiner—Timothy M. McMahon
Attorney, Agent, or Firm—Merchant, Gould, Smith, Edell, Welter & Schmidt

[57] ABSTRACT

An ultra-violet flashlight comprising a housing containing an ultra-violet light source, a power source, an on-/off switch and a gravity switch, whereby the ultra-violet light source is activated by turning on the on/off switch and directing the flashlight in a downward position relative to the ultra-violet light source and a method for instantly sterilizing objects with which a person comes in contact comprising passing over said objects ultra-violet radiation from said flashlight.

3 Claims, 1 Drawing Sheet

U.S. Patent      Aug. 28, 1990      4,952,369
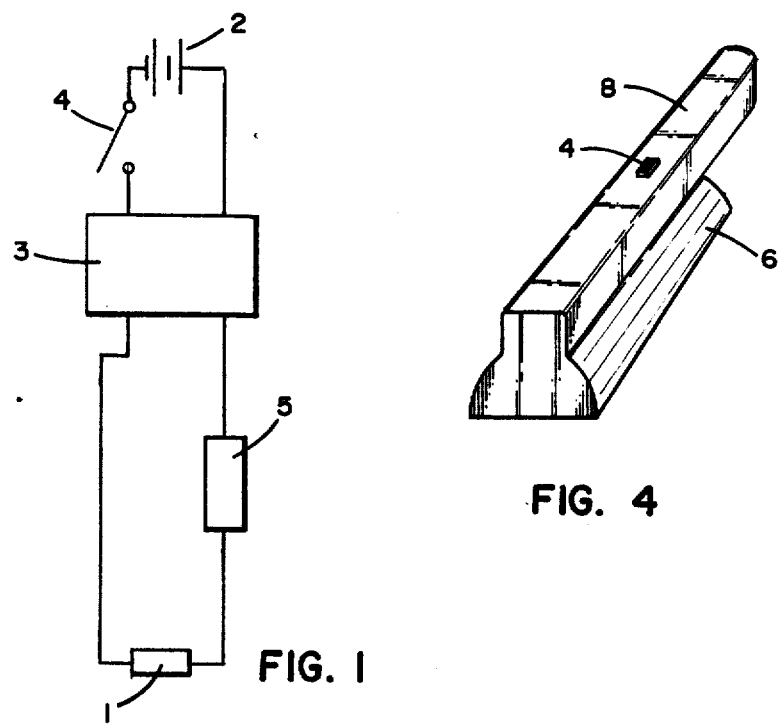
FIG. 4
FIG. 1
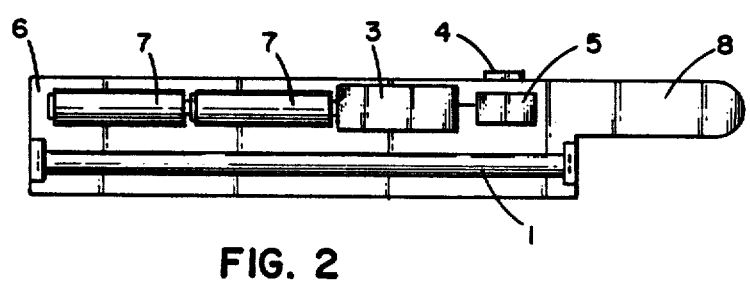
FIG. 2
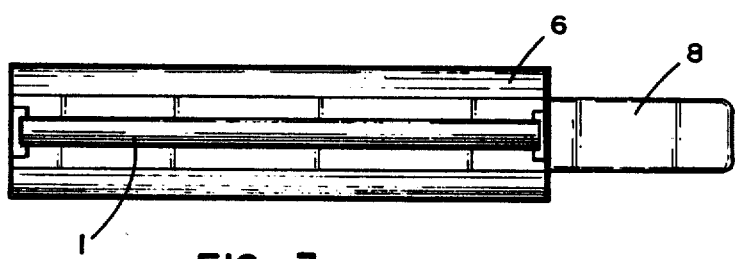
FIG. 3

ULTRAVIOLET DEVICE AND ITS USE

The present invention concerns a portable ultra-violet lamp, more specifically an ultra-violet flashlight.

Ultra-violet rays are known to kill germs and viruses, thus operating rooms have ultra-violet lamps in order to provide suitable sterile conditions. Ultra-violet lights are also placed in front of the doors to operating rooms to disinfect the persons entering the same. Ultra-violet light has also been used to sterilise water, as in water filtration systems. One of the major advantages of using ultra-violet light is that it is effective very quickly and in a matter of seconds or fractions thereof the area exposed to ultra-violet light is sterilised.

It is the object of the present invention to provide a portable pocket-size ultra-violet flashlight, which can be used by ordinary individuals to sterilise objects such as toilet seats, flatware in restaurants, public telephones and kitchen counter tops, among other things.

Ultra-violet light is known to be harmful to the eyes and therefore it is an object of the present invention to provide a pocket ultra-violet light which is activated only when the ultra-violet lamp is pointed downwards.

In accordance with this invention there is provided a hand-portable ultra-violet flashlight, comprising a housing containing an ultra-violet light source, a power source, an on/off switch and a gravity switch, wherein the ultra-violet light source is activated when turning the on/off switch to the on position only when the light source is facing downward. The ultra-violet lamp of this invention may also be provided with a converter, which will convert battery power to a higher voltage suitable for certain ultra-violet lamps.

The invention will now be described in detail with reference to the following figures:

FIG. 1 shows a circuit diagram of the invention;

FIG. 2 is a cross-sectional view of one embodiment of the invention;

FIG. 3 is a view from the bottom of the embodiment of FIG. 2; and

FIG. 4 is a perspective view of the ultra-violet pocket flashlight.

Referring now to FIG. 1, this shows the ultra-violet light source 1 connected to a power supply 2 via a converter 3 which increases the voltage from the power supply, which may be ordinary batteries such as 1.5 volt DC batteries, and converts these to 12 volt AC power. The lamp 1 is activated when the on/off switch 4 is closed and the lamp is facing downward, since the gravity switch 5 breaks the circuit if the lamp is not facing down. In principle, the ultra-violet lamp can be any type of light source generating ultra-violet light in sufficient intensity to disinfect objects at relatively short distances.

One contemplated embodiment is shown in FIGS. 2–4, wherein the elongated ultra-violet lamp 1 is enclosed in a housing 6, said housing also contains ordinary batteries 7, a converter 3, an on/off switch 4 and a gravity switch 5. A handle 8 may extend from the housing for convenient holding of the portable flashlight.

It is of course understood that this invention is not limited to the particular embodiment shown in the FIGS. 2–4. Other shapes and dimensions for such portable ultra-violet pocket lamps can be readily manufactured and are within the scope of this invention.

What is claimed:

1. A hand-portable pocket-size ultra-violet flashlight, comprising a housing containing an ultra-violet light source, a power source, an on/off switch and a gravity switch which are electrically interconnected in an electric circuit which can be broken by either or both of the respective switches, whereby the ultra-violet light source is activated by turning on the on/off switch and directing the flashlight in a downward position relative to the ultra-violet light source.

2. A flashlight in accordance with claim 1 containing a power converter adapted to increase the voltage from the power supply to the ultra-violet light source.

3. A method for sterilising objects with which a person comes in contact comprising passing over said objects with ultra-violet radiation from a flashlight, said flashlight including a housing containing an ultra-violet light source, a power source, an on/off switch and a gravity switch which are electrically interconnected in an electric circuit which can be broken by either or both of the respective switches, whereby the ultra-violet light source is activated by turning on the on/off switch and directing the flashlight in a downward position relative to the ultra-violet light source.

* * * * *